United States Patent [19]

Stankoff

[11] 4,134,059
[45] Jan. 9, 1979

[54] METHOD AND APPARATUS FOR MEASURING THE CORROSION CURRENT OF AN IMMERSED STRUCTURE PROVIDED WITH A CATHODIC PROTECTION DEVICE

[75] Inventor: Alain Stankoff, Clamart, France

[73] Assignee: Societe Intersub Developpement, France

[21] Appl. No.: 804,315

[22] Filed: Jun. 7, 1977

[30] Foreign Application Priority Data

Jun. 10, 1976 [FR] France .................................. 76 17601

[51] Int. Cl.² ............................................. G01N 27/42
[52] U.S. Cl. ................................ 324/29; 324/65 CR; 324/118; 324/127
[58] Field of Search ............... 324/29, 30 R, 30 A, 324/1, 65 CR, 120, 127, 118; 204/195 R, 195 C

[56] References Cited

U.S. PATENT DOCUMENTS

| | | | |
|---|---|---|---|
| 2,297,568 | 9/1942 | Leonardon | 324/1 |
| 2,802,182 | 8/1957 | Godshalk et al. | 324/127 |
| 2,820,947 | 1/1958 | Gunn | 324/118 |
| 2,839,722 | 6/1958 | Marsh | 324/65 CR |

*Primary Examiner*—M. Tokar
*Attorney, Agent, or Firm*—DeLio and Montgomery

[57] ABSTRACT

The invention relates to a method and apparatus for measuring the corrosion current of an elongated structure immersed in a fluid and provided with a cathodic protection device, the apparatus comprising at least one closed magnetic circuit immersed in the fluid and orientated so that a certain amount of electric current can pass therethrough, a coil on this magnetic circuit, measuring means connected to the terminals of this coil and modulation means (perforated rotating disc) for periodically varying, in time, the quantity of electric current circulating through the magnetic circuit. The invention is applied more particularly to the surveillance of underwater pipe-lines.

7 Claims, 4 Drawing Figures

METHOD AND APPARATUS FOR MEASURING THE CORROSION CURRENT OF AN IMMERSED STRUCTURE PROVIDED WITH A CATHODIC PROTECTION DEVICE

The present invention relates to a method for measuring the corrosion current of an immersed elongated structure provided with a cathodic protection device comprising protection anodes, and more particularly, to a method for measuring the corrosion current of an underwater pipeline provided with sacrificial anodes for cathodic protection.

The invention also relates to an apparatus for measuring one or more components, in a determined direction, of a density of electric current circulating in a fluid.

It is known to protect an underwater pipeline (generally made of iron or ferrous metal) from corrosion by coating it with a water-tight coating layer and providing it with sacrificial anodes made of zinc or aluminium which are electrically connected to the pipeline and which are in direct contact with the sea water. Such anodes constitute, with the sea water and the pipeline, an electric cell ensuring a cathodic polarization of the pipeline, with the result that, in the case of failure of the coating layer of the pipeline, a rapid corrosion of said latter by the sea water is avoided. This result is obtained due to the establishment of an electric current between the anode and the part of pipeline accidentally in contact with the sea water.

However, this electrical current causes wear of the anode; it is therefore necessary to watch over the state of corrosion of the pipeline and the state of wear of its protection anodes.

It is a particular object of the invention to propose a method enabling not only the rate of wear of the anodes to be known, but also the parts, where the pipeline is the seat of intense corrosion, to be located.

To this end, in accordance with the invention, the value of at least one component of the vector-density of corrosion current is measured at each point along a section of pipeline located between two adjacent anodes.

In this way, it is easy to deduce from this measurement, by a prior standardization, the value of the total current circulating between an anode and the pipeline. This value of total current makes it possible to know the rate of wear of the anode and, consequently, the moment when it will be necessary to replace this anode by a new one.

This measurement also enables the parts where the pipeline is the seat of intense corrosion to be located. In fact, at such spots, the pipeline receives an abnormally high current density.

For measuring a component, in a determined direction, of the density of corrosion current, it is advantageous to use an apparatus according to the present invention. This apparatus comprises, according to the invention, at least one magnetic circuit immersed in the sea water and orientated so that a certain amount of corrosion current of the pipeline can pass therethrough, a coil provided on this magnetic circuit, means for measuring an electric signal present at the terminals of this coil and modulation means for periodically varying, in time, the value of the electric current circulating through the magnetic circuit and inducing a signal in the winding.

The modulation means are advantageously constituted by an electrically insulating disc, rotating about an axis perpendicular to its plane, said disc being provided with at least one opening which is offset with respect to said axis of rotation, and being arranged with respect to the magnetic circuit so as to be able, periodically, to vary the section of passage of the electric current circulating through the magnetic circuit.

This apparatus presents the following advantages:

it is of simple design;
it enables the magnetic field of the earth to be eliminated;
as the sea water offers little resistance to the rotation of the modulator disc, said latter may rotate at high speeds, with the result that the signal-to-noise ratio of this apparatus may be increased;
by using a plurality of magnetic circuits and by arranging a plurality of openings in the modulator disc, the modulation frequency may be further increased and the signal-to-noise ratio of the apparatus therefore improved.

The invention will be more readily understood on reading the following description with reference to the accompanying drawings, in which:

FIG. 1 schematically shows the corrosion currents established between two adjacent anodes and an underwater pipeline provided with these anodes;

Figure 1:
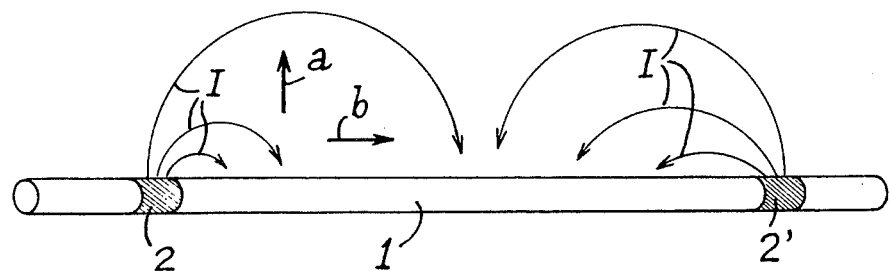

Referring now to the drawings, FIG. 1 shows an underwater pipeline 1 made of iron coated with a water-tight coating layer. The pipeline is provided with anodes 2, 2' made of zinc, in sleeve form, regularly spaced along the pipeline.

Between the anodes 2 and pipeline 1 are established currents I of relatively low intensity under normal conditions, leaving anodes 2,2' and regularly arriving, with a substantially uniform density, over the whole length of the section of pipeline from one anode to the next.

Figure 2A:
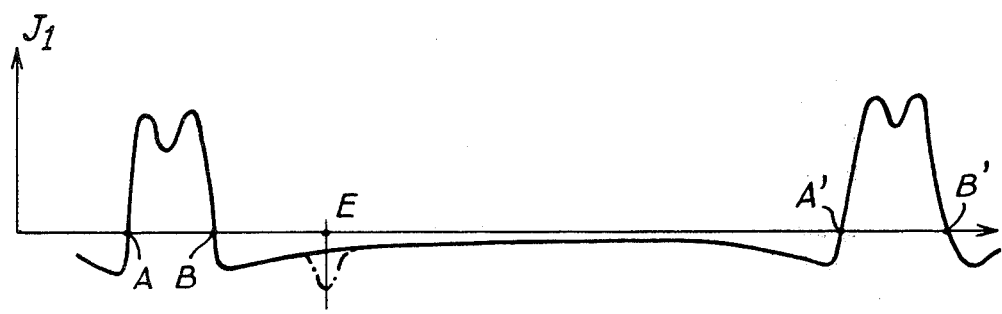
FIG. 2a shows a diagram of the variation along the pipeline of FIG. 1 of the component, perpendicular to the axis of the pipeline, of the density of the corrosion currents of FIG. 1.

FIG. 2a shows the variation, along this section of pipeline, of the component $J_1$, in the direction "a" which is centrifugal and perpendicular with respect to the axis of the pipeline, of the current density.

This Figure shows that this density $J_1$ is positive and relatively high at the anodes 2 and 2', on the abscissa between A and B, and A' and B' and that it is relatively low, negative and substantially uniform over the whole section of pipeline from one anode to the next, corresponding to that part of the abscissa located between points B and A'.

Figure 2B:
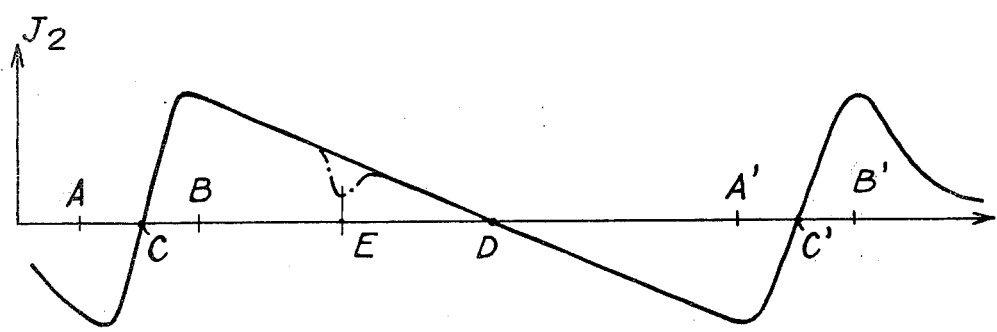
FIG. 2b shows a diagram of the variation along the pipeline of FIG. 1 of the component, parallel to the axis of the pipeline, of the density of the corrosion currents of FIG. 1, and FIG. 3 schematically shows an apparatus for measuring the current density according to an embodiment of the invention.

FIG. 2b shows the variation, along the pipeline, of the component $J_2$, in the direction "b" which is parallel to the axis of the pipeline and directed from left to right in FIG. 1, of the density of corrosion current.

FIG. 2b shows that this current density $J_2$ is positive between a point on the abscissa, C, located at the centre of segment AB and a point on the abscissa, D, corresponding to the centre of the section of pipeline located between anodes 2 and 2'. At points C and D, the current density $J_2$ is zero.

This density $J_2$ is negative between point D and point C', homologous to point C and corresponding to segment A'B'.

It is simple, by a prior standardization, to deduce from the information supplied by at least one of the variation curves shown in FIGS. 2a and 2b, the value of the total current circulating between an anode 2 and the pipeline 1.

A zone of intense corrosion of the pipeline centred at point of abscissa E causes curve distortions as shown in broken lines in FIG. 2a and 2b. These zones of intense corrosion are therefore easily detected by the measurements of the current densities $J_1$ and $J_2$ made over the whole length of the pipeline.

An unbalance between the state of wear of adjacent anodes 2 and 2' and/or a difference between the state of corrosion of the two halves of the section of pipeline located between anodes 2 and 2', are translated by a displacement of the point D of zero current density $J_2$ to the left or to the right in FIG. 2b.

Figure 3:
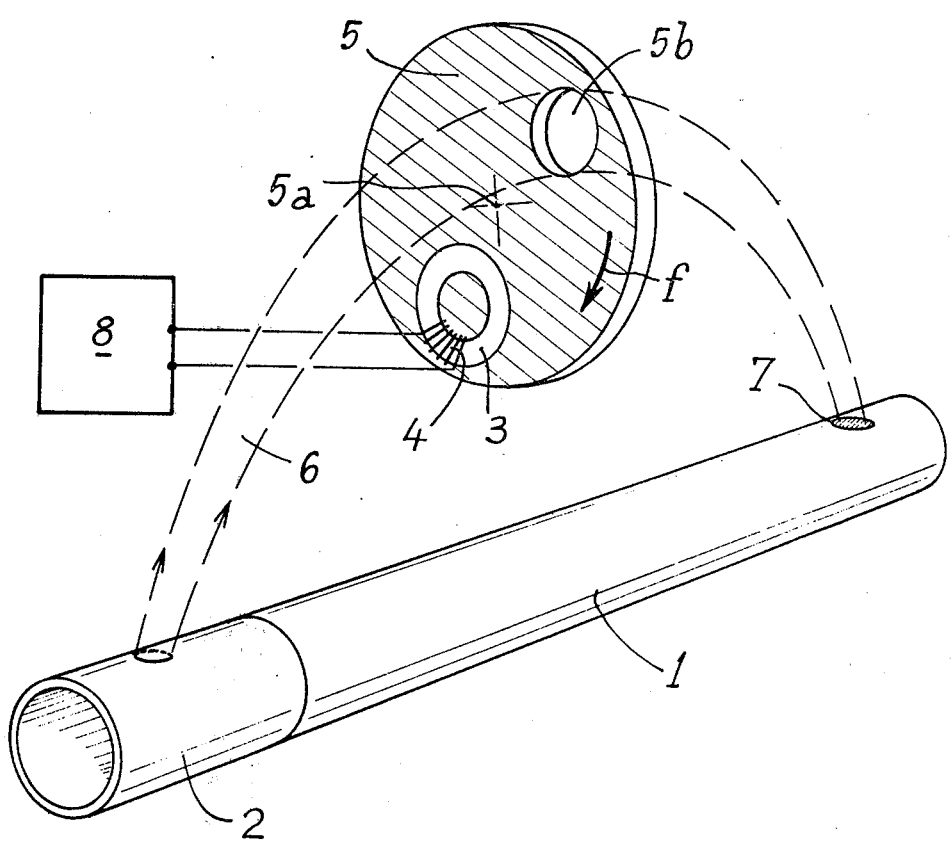

The apparatus shown in FIG. 3 makes it possible to measure a density of direct current circulating in a fluid, for example a density of corrosion current circulating in sea water around a pipeline 1 provided with anodes 2. The apparatus comprises a doughnut 3 made of magnetic material on which a measurement coil 4 is provided. A disc 5 made of electrically insulating material, parallel to the plane of the doughnut 3, is placed against this latter so as to be able to oppose the passage of the D.C. corrosion current 6 through the doughnut 3. The disc 5 rotates (arrow f) about an axis perpendicular to its plane and passing through its centre 5a. An offset circular opening 5b is made in the disc 5 and is so dimensioned as to be able to be superposed periodically on the central opening of the doughnut 3.

In this way, this apparatus makes it possible to measure the component, in the direction perpendicular to the plane of doughnut 3, of the density of corrosion current establishing between the anode 2 and the pipeline 1 and, in particular, between the anode 2 and a zone 7 of intense corrosion on the pipeline 1.

This current density is in fact the intensity of the current 6 which may pass through the central opening of the doughnut 3. The rotation of the disc 5 obtained by a drive means (not shown) modulates the current 6 passing through the doughnut 3, so that an electromotive force is induced in the measurement coil 4. An apparatus 8, connected to the terminals of this coil 4, enables this electromotive force to be measured.

The doughnut 3 is advantageously premagnetized near the maximum of its differential magnetic permeability. In this way, the apparatus is more sensitive.

The input impedance of the apparatus 8 is advantageously sufficiently low for the amount of current passing through the doughnut 3 to be more than 10% of the quantity of current which would pass through the doughnut 3 if the latter were not made of magnetic material.

What we claim is:

1. A method of watching over the state of corrosion of an immersed elongated metallic structure provided with cathodic protection means comprising protection anodes, and of watching over the rate of wear of one of said anodes, comprising the steps of measuring the density of direct electrical current at each point along the axis of the structure, and locating a local relative extremum in the current density between adjacent anodes, thereby locating a point of relatively intense corrosion of the structure and deducing by a prior standardization the total current circulating between an anode and the structure.

2. A method of watching over the state of corrosion of an immersed elongated metallic structure provided with cathodic protection means comprising protection anodes, and of watching over the rate of wear of one of said anodes, comprising the steps of measuring a component, oriented in a predetermined direction with respect to the axis of the structure, of the density of direct electrical current at each point along the axis of the structure, and locating a local relative extremum in said component of the current density between adjacent anodes, thereby locating a point of relatively intense corrosion of the structure and deducing by a prior standardization the total current circulating between an anode and the structure.

3. A method according to claim 2, wherein said component of the density of direct electrical current is measured by causing the electrical current to pass through the aperture of a magnetic coil, varying periodically in time the area of this aperture, and measuring the variation in time of the magnetic flux circulating the coil.

4. Apparatus for measuring one component of density of electrical current circulating in a fluid comprising at least one closed magnetic circuit immersed in the fluid oriented to permit the electrical current to pass therethrough, a measuring coil associated with the magnetic circuit, means for measuring an electric signal associated with said measuring coil, and modulation means for periodically varying, in time, the quantity of electric current circulating through the magnetic circuit.

5. An apparatus as claimed in claim 4, wherein the modulation means are constituted by an electrically insulating obturator member which may be periodically interposed on the path of the electric current through the magnetic circuit.

6. An apparatus as claimed in either one of claim 4 wherein the modulation means are constituted by a disc rotating about an axis perpendicular to its plane, this disc being provided with at least one opening offset with respect to the axis of rotation and being arranged with respect to the magnetic circuit so that the section of passage of the electric current through said magnetic circuit can be periodically varied.

7. An apparatus as claimed in claim 4, wherein the electric signal measuring means have a sufficiently low input impedance for the amount of current passing through the magnetic circuit to be more than 10% of the amount of current which would pass through a solid identical to the magnetic circuit but made of non-magnetic material.

* * * * *